United States Patent [19]

Robirds

[11] Patent Number: 5,377,804
[45] Date of Patent: Jan. 3, 1995

[54] MOISTURE DETECTING AND POWER SHUT OFF APPARATUS FOR BILL VALIDATORS, COIN MECHANISMS AND THE LIKE

[76] Inventor: David C. Robirds, 809 Briarwood, Abilene, Tex. 79603

[21] Appl. No.: 963,722

[22] Filed: Oct. 21, 1992

[51] Int. Cl.⁶ .................................................. G07F 9/02
[52] U.S. Cl. ...................................... 194/202; 194/348
[58] Field of Search ................ 194/200, 201, 202, 348

[56] References Cited

U.S. PATENT DOCUMENTS 5,156,250  10/1992  Parish et al. .......................... 194/348

FOREIGN PATENT DOCUMENTS 1-250189  10/1989  Japan ................................... 194/348
2-118795   5/1990  Japan ................................... 194/348
2-287792  11/1990  Japan ................................... 194/348
4-42387    2/1992  Japan ................................... 194/348

*Primary Examiner*—F. J. Bartuska

[57] ABSTRACT

The present invention is a moisture-detecting apparatus for bill validators and coin mechanisms used in vending machines. Vandalism by "salting" of these types of machines results in loss of product, monies, and damage to the mechanisms. Therefore the reason for the present invention. Which consist of moisture-detecting probes and the ability to instantly shut off the logic lines and power to the bill validator, stopping damage to the bill validator, power supply, and coin mechanism power side. Thereby stopping the "jack pot" rejecting effect of coins, and the free vending of products, when moisture is detected.

4 Claims, 2 Drawing Sheets

MOISTURE DETECTING AND POWER SHUT OFF APPARATUS FOR BILL VALIDATORS, COIN MECHANISMS AND THE LIKE

BACKGROUND OF THE INVENTION

Recorded history, traces the vending machine back to about 215 B.C. and is thought to have been invented by mathematician, Hero or his teacher Tesibius. Both were natives of Greece, Hero's original manuscript described and illustrated a coin-activated device for vending sacrificial water in Egyptian temples. The device was completely automatic and was set in operation by the insertion of "a coin of five drachmas."

From its modest beginning, this silent salesman with built-in cash register has been adapted for a wide variety of goods and services, and today these machines annually move billions of dollars of goods and services to consumers around the world.

Unfortunately, with the development of the vending machine, the public at large has come to regard the silent salesman as fair game—to "beat" the machine or, failing that, to stuff or pour something down its innards to put it out of commission. Reckoning with this perversity is still a mighty challenge for inventors, designers and engineers.

Which brings us to the purpose of the present invention. The latest technology used to "beat" these machines, and more particular, machines having bill validators, is the injection of foreign liquids into the bill validators. This method is better known as "salting" the machine.

When a bill validator or coin mechanism is vandalized by conductive liquid, it causes a short in the power supply and logic signal pins. The shorting of the power supply causes an increase in current, causing major damage to the power supply, at the same time the logic pins are shorted together sending false signals to the bill validator and coin mechanism telling them to give back change and/or vend.

The present invention immediately shuts off the logic lines and power to the bill validator and coin mechanism when the vending machine is "salted" wherein, the probe instantly detects any conductive liquid which activates the apparatus.

SUMMARY OF THE INVENTION

Vandalism of vending machines has been a problem ever since they were put into use. The most recent form of vandalism is the injection of conductive liquid, such as salt water, into the bill validators and coin mechanism. This method of vandalism is called "salting" and is a problem throughout the industry. Resulting in millions of dollars in loss of products, repairs, and money.

The present invention addresses the problems of "salting," by providing a cost effect moisture detecting apparatus. Therein when a bill validator or coin mechanism is "salted," it is an object of the present invention; to provide an effective method of detecting the presence of moisture, wherein electronic moisture-detecting probes are utilized.

Another object of the present invention is, once the probe detects moisture in either the bill validator or coin mechanism it instantly shuts down the power circuits to the bill validator and coin mechanism, thereby greatly reducing the risk of damage to the bill validator or coin mechanism control power circuits.

A still further object of the present invention is to eliminate the "jack potting" of the coin mechanism.

Yet another object of the present invention is to eliminate free vending that is caused due to salting vandalism.

Figure 1:
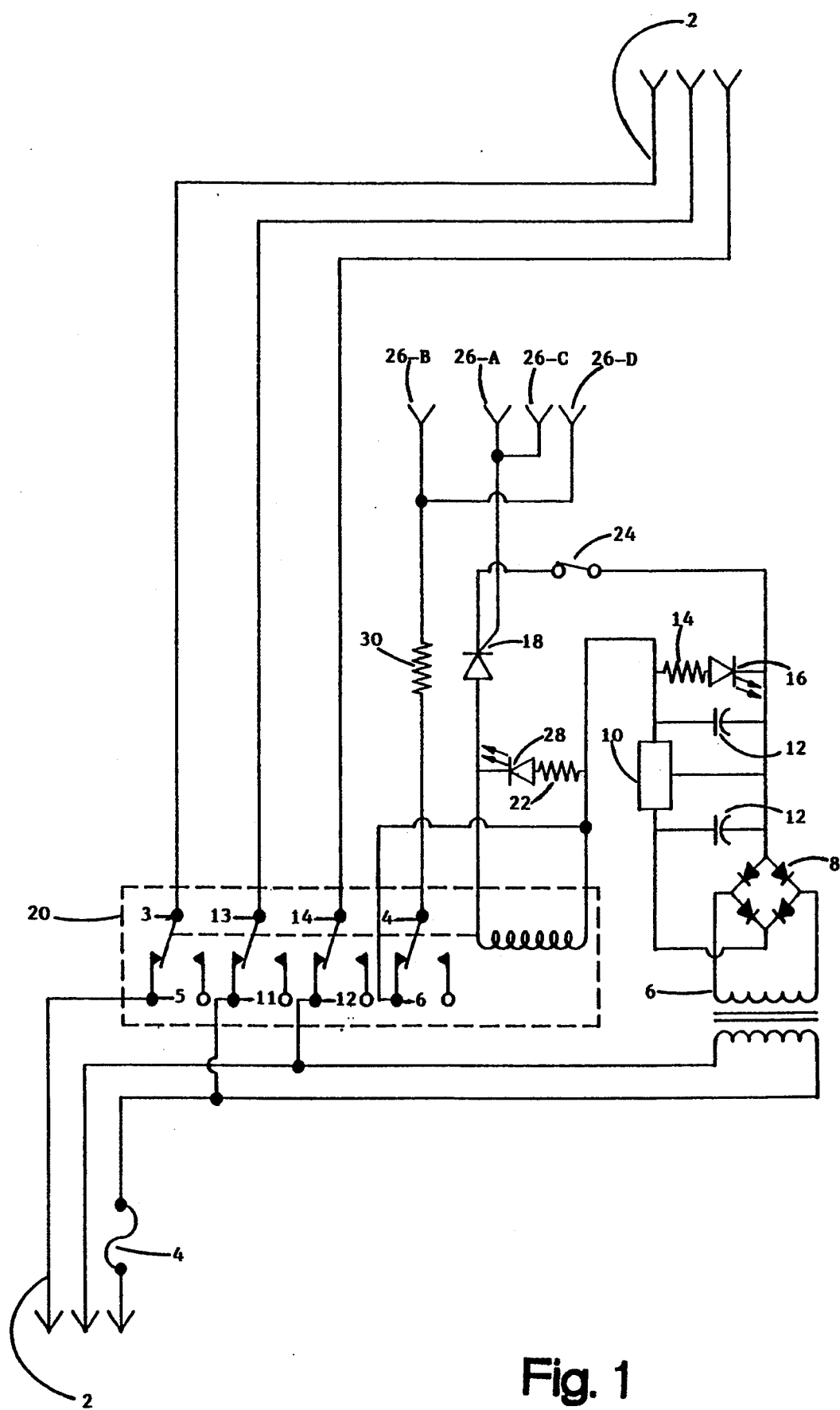
FIG. 1 is a schematic of a moisture-detecting apparatus tot bill validators and coin mechanisms.
Figure 2:
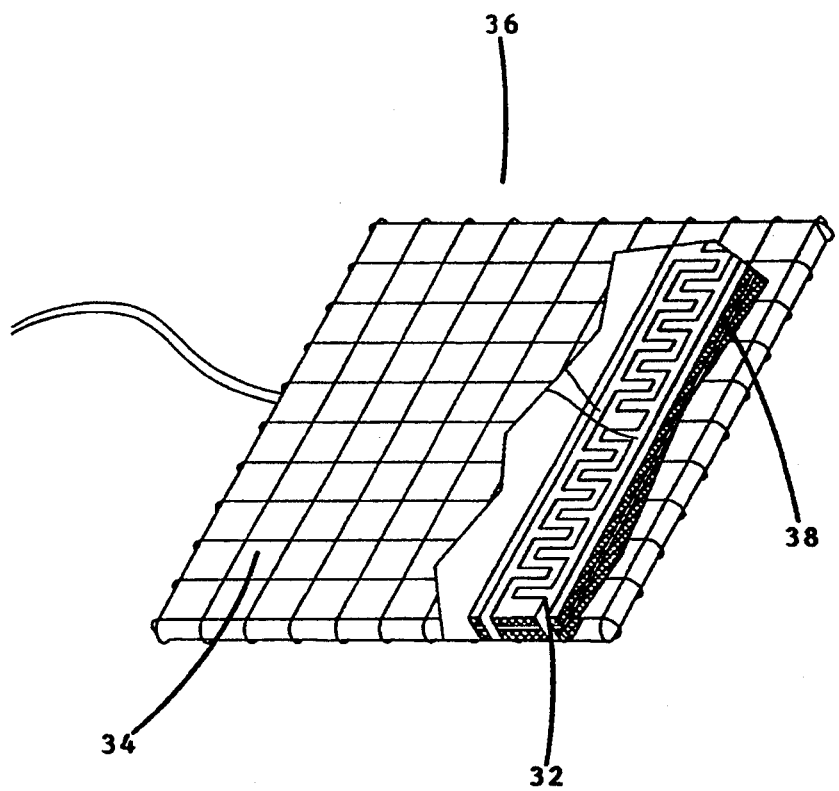
FIG. 2 is a cut-a-way view of the moisture-sensing probe showing the zig-zag copper foil folded over and around a circuit board.

NUMERAL REFERENCE LIST 2 twelve-conductor cable
4 fuse
6 transformer
8 full wave bridge rectifier
10 regulator
12 capacitor
14 resistor
16 L.E.D.
18 S.C.R. (silicon-controlled rectifier)
20 four pole, double throw polarized relay
22 resistor
24 switch
26 four pin socket
   26-A receptacle
   26-B receptacle
   26-C receptacle
   26-D receptacle
28 L.E.D.
30 resistor
32 zig-zag copper foil
34 non-metallic fabric
36 moisture-sensing probe
38 circuit board

DETAILED DESCRIPTION OF THE PREFERRED EMBODIMENT

Operation of the Invention

I. Power Supply

The power supply draws its operating voltage directly from the vending machine. The 110 volts alternating current (AC) voltage passes through fuse (4) and is applied to transformer (6). The purpose of fuse (4) is to protect the other components in the device in the event of a malfunction. Transformer (6) accepts 110 volts alternating current (AC) into its primary winding and produces 12.6 volts AC out of its secondary winding. This 12.6 volts AC then goes to full wave bridge rectifier (8) which converts the 12.6 volts AC voltage into 12.6 volts pulsating direct current (DC) voltage. The 12.6 volts pulsating voltage then goes through capacitor (12) which partially smooths the pulsations. From capacitor (12) the 12.6 pulsating voltage passes through voltage regulator (10) and emerges as regulated 12 volts DC. The regulated 12 volts DC passes through capacitor (12) which smooths out any remaining pulsations. L.E.D. (16) is a DC power-on indicator light and will be illuminated so long as AC and DC power are both present. Resistor (14) is a voltage-dropping resistor to protect L.E.D. (16).

II. Control Circuit

The regulated 12 volts DC is applied to the moisture-detection probe and the control portion of the device.

When the control portion of the device is in its de-energized (quiescent) state, silicon controlled rectifier S.C.R. (18) is not conducting current, L.E.D. (28) is off, resistor (22) has no current flowing through it, relay (20) is de-energized, switch (24) is closed, and resistor (30) has no current flowing through it. Relay (20) is a four pole double throw relay. In its de-energized condition all four relay armatures are made to the four normally closed contacts. Three of these contacts have signals and voltages coming from the vending machine and going to the coin mechanism and bill validator. The other armature and contact provide 12 volts DC voltage to the moisture-sensing probe 36.

When the moisture-sensing probe 36 detects the presence of any electrically-conductive fluid, it provides a voltage to the gate of the S.C.R (18) which turns the S.C.R. (18) on. When the S.C.R. (18) is on, it allows current to flow through L.E.D. (28), resistor (22), relay (20) and switch (24). L.E.D. (28) turns on indicating the circuit is energized. Resistor (22) is a voltage-dropping resistor to protect L.E.D. (28). When current flows S.C.R. (18) it allows current to flow in the winding of relay (20) thus energizing relay (20). With relay (20) energized, the four armatures are made to the four normally open contacts which removes the control signals and voltages from the coin mechanism and bill validator thus preventing any electrical damage to these units caused by the introduction of salt water or other electrically-conductive fluid.

III. Moisture-Sensing Probe

The moisture-sensing probe 36 is comprised of a strip of copper foil which has a 1 millimeter wide zig-zag groove etched across the middle thus creating two electrically isolated copper strips 32. These two strips 32 are folded over 180 degrees and form in effect a double-sided moisture-sensing probe 36. This probe 36 is enclosed by a non-metallic perforated fabric 34 such as nylon mesh.

The present invention is separated into three circuits: A: The Power Circuit; B: The Control Circuit, and; C: The Sensing Circuit.

The Power Circuit is separated from the Control Circuit, but is electronically connected by Conductor Cable 2. The Power Circuit is contained in a separate housing (not shown). Components contained in the Power Circuit Housing are; an eight-pin jones socket (not shown), fuse 4, transformer 6, full wave bridge rectifier 8, voltage regulator 10, two electrolytic capacitors 12, one resistor 14, and one green L.E.D. 16. The twelve-conductor cable connects the Power Circuit Housing to the Control Circuit Housing. The Control Circuit Housing (not shown) consists of an eight-pin jones plug (not shown), S.C.R. (silicon-controlled rectifier) 18, four pole double throw relay 20, two resistors 22 and 30, one normally closed, momentarily open switch 24, and a four-conductor socket 26 for the probe. The Sensing Circuit consists of the probe 36. The probe 36 is constructed of two parallel copper strips 32 on a circuit board 38 separated by a millimeter space. The probe consists of a front, back, and four sides, giving it a sensing capability of a full 360 degrees. In addition, the probe 36 is completely covered with a non-metallic perforated fabric 34 such as nylon mesh or like material, thus preventing metallic objects from activating the circuit. In addition, the perforated fabric 34 retains the moisture, thereby preventing premature resetting which could result in damage to the protected electronic circuitry.

ASSEMBLY: Starting with approximately twelve inches of color-coded twelve-conductor cable and an eight-pin jones plug, solder one wire of the twelve-conductor cable, such as the blue wire to pin one of the jones plug which is AC hot, cut this wire approximately two inches from the solder connection then solder the blue wire from pin one to one side of fuse holder 4, solder the blue wire of the twelve-conductor cable which was cut, to the opposite side of fuse holder 4. This wire continues to the primary side of transformer 6 where it is soldered. Solder a separate wire from the twelve-conductor cable such as the brown wire to pin two (neutral) of the eight-pin jones plug, solder connect to the opposite side of transformer 6. Solder connect the full wave bridge rectifier 8 to the secondary side of transformer 6 (this converts the A.C. voltage to D.C. voltage). Solder connect the positive side of the capacitor 12 to the positive output of full wave bridge rectifier 8, solder connect the negative side of capacitor 12 to the negative output of full wave bridge rectifier 8, solder connect the positive output of the full wave bridge rectifier to the input voltage regulator 10, solder connect the ground of the voltage regulator 10 to the negative output of full wave bridge rectifier 8, the positive side of the second capacitor 12 is solder connected to the output of the voltage regulator 10, the negative side of capacitor 12 is solder connected to the negative output of the full wave bridge rectifier 8.

The cathode of the L.E.D. 16 is solder connected to the negative output of the full wave bridge rectifier 8, the anode of the L.E.D. 16 is solder connected to the 1K OHM resistor 14, the 1K OHM resistor 14 is solder connected to the output of the regulator 10. Solder connect one wire of the twelve conductor cable, such as the purple wire to the output of voltage regulator 10, solder connect the opposite end of the purple wire to the positive side of relay 20. Using another wire from the twelve conductor cable, such as the green wire, solder the green wire to the negative output of the full wave bridge rectifier 8, solder connect the opposite end of the green wire to one side of the switch 24. A jumper wire is solder connected to the opposite side of switch 24 and solder connected to the cathode of the S.C.R. 18. Solder connect the anode of the S.C.R. 18 to the negative side of relay 20. The cathode of L.E.D. 28 is solder connected to the negative side of relay 20. The anode is solder connected to a 1K OHM resistor 22 and solder connected to the positive side of relay 20. The gate of the S.C.R. 18 is connected to receptacle 26-A and 26-C of the four conductor socket 26, solder connect the 100 OHM resistor 30 to pin four of relay 20, on the opposite side of the 100 OHM resistor 30, solder connect a jumper wire to receptacle 26-B and 26-D of the four conductor socket 26. Solder connect a jumper wire from pin 6 of the relay 20 to the positive side of relay 20. From the transformer side of fuse 4 solder connect a jumper wire pin 11 of relay 20.

Using a separate wire of the twelve conductor cable, such as red. Solder connect the red wire to pin 13 of relay 20 then solder connect the opposite end of the red wire to pin one of the eight-pin jones socket. Solder connect a jumper wire from pin two (neutral) line, of the eight-pin jones plug and solder connect the opposite end of the jumper wire to pin twelve of relay 20. Using another separate wire from the twelve conductor cable, such as the black wire. Solder connect the black wire to pin fourteen of relay 20, then solder connect the opposite end of the black wire to pin two of the eight-pin jones socket. Solder connect a jumper wire from pin six of the eight-pin jones plug (this is the blocker signal) to pin five of relay 20. Using another separate wire of the twelve-conductor cable, such as an orange wire, solder connect the orange wire to pin three of relay 20, and solder connect the opposite end to pin six of the eight-pin jones socket. Using another separate wire of the twelve-conductor cable, such as yellow. Solder connect the yellow wire to pin three of the eight-pin jones plug and solder connect the opposite end to pin three of the eight-pin jones socket. Picking still another separate wire of the twelve-conductor cable, such as gray. Solder connect the gray wire to pin five of the eight-pin jones plug and solder connect the opposite end to the pin five of the eight-pin jones socket. Choosing another separate wire of the twelve-conductor cable, such as white. Solder connect the white wire to pin seven of the eight-pin jones plug, and solder connect the opposite end to pin seven of the eight-pin jones socket.

Using still another separate wire of the twelve-conductor cable, such as tan. Solder connect the tan wire to pin eight of the eight-pin jones plug, and solder connect the opposite end to pin eight of the eight-pin jones socket.

Having thus described and disclosed my invention in detail, it should be appreciated that while the preferred embodiments of the present invention have been described herein in specific and complete detail, numerous modifications in, additions to, and omissions of said details are possible within the intended spirit and scope of the invention.

I claim:

1. A moisture detecting and power shut-off apparatus a vending machine which includes a bill validator and a coin mechanism, the apparatus comprising:

an S.C.R. (silicon-controlled rectifier), a relay and means for detecting moisture;

said means for detecting moisture is comprised of an electronic probe having a main strip of copper foil which has a one millimeter wide zig-zag groove etched across the middle thus creating two electrically isolated copper strips, said copper strips are folded over and around a circuit board 180 degrees, and, form in effect a 360 degree double-sided moisture-sensing probe;

said moisture-sensing probe is activated by the presence any electrically-conductive fluid, thereby energizing the S.C.R. which in turn allows current to flow into the relay, thus activating the normally closed contacts of the relay, thereby opening the contacts, and shutting-off the power to the bill validator and coin mechanism.

2. The moisture detecting and power shut-off apparatus as defined in claim 1 wherein said apparatus having means shutting-off power to the above said vending machine.

3. The moisture detecting and power shut-oil apparatus as defined in claim 1 wherein said apparatus having means shutting-off power to the moisture detecting probe.

4. The moisture detecting and power shut-off apparatus as defined in claim 1 wherein said apparatus having means resetting the apparatus.

* * * * *